United States Patent [19]
Ferrara et al.

[11] Patent Number: 5,462,059
[45] Date of Patent: Oct. 31, 1995

[54] METHOD FOR ASSESSING AND DISPLAYING VASCULAR ARCHITECTURE USING ULTRASOUND

[75] Inventors: Katherine W. Ferrara, New York, N.Y.; V. Ralph Algazi, Davis, Calif.

[73] Assignee: The Regents of the University of California, Oakland, Calif.

[21] Appl. No.: 248,824

[22] Filed: May 25, 1994

[51] Int. Cl.$^6$ ........................................ A61B 8/06
[52] U.S. Cl. ........................................ 128/661.09
[58] Field of Search ............ 128/661.05, 661.08–661.10

[56] References Cited

U.S. PATENT DOCUMENTS

| | | |
|---|---|---|
| 3,771,355 | 11/1973 | Sachs . |
| 4,062,237 | 12/1977 | Fox . |
| 4,074,564 | 2/1978 | Anderson . |
| 4,265,126 | 5/1981 | Papadofrangakis et al. . |
| 4,276,885 | 7/1981 | Tickner et al. . |
| 4,431,936 | 2/1984 | Fu et al. . |
| 4,519,260 | 5/1985 | Fu et al. . |
| 4,530,363 | 7/1985 | Brisken . |
| 4,542,744 | 9/1985 | Barnes et al. . |
| 4,580,574 | 4/1986 | Gavish . |
| 4,759,375 | 7/1988 | Namekawa . |
| 4,790,323 | 12/1988 | Leavitt et al. . |
| 4,932,415 | 6/1990 | Angelsen et al. . |
| 5,000,184 | 3/1991 | Bonnefous . |
| 5,062,430 | 11/1991 | Bonnefous . |
| 5,109,856 | 5/1992 | Bonnefous et al. . |
| 5,109,857 | 5/1992 | Roundhill et al. . |
| 5,201,313 | 4/1993 | Katakura . |
| 5,233,994 | 8/1993 | Shmulewitz . |
| 5,243,988 | 9/1993 | Sieben et al. . |
| 5,329,924 | 7/1994 | Sato et al. ................ 128/661.09 X |
| 5,349,524 | 9/1994 | Daft et al. ................ 128/661.08 X |
| 5,363,851 | 11/1994 | Hall et al. ................ 128/661.09 |

OTHER PUBLICATIONS

Sollish (1977) Ultrason. Tissue Charac. Linzer, ed. pp. 53–56.
Chivers et al. (1973) 2nd World Cong. Ultrasonics Med. 300–303.
Huggins et al. (1977) Ultra. in Med & Biol. 2(4):271–277.

Primary Examiner—Francis Jaworski
Attorney, Agent, or Firm—John P. O'Banion

[57] ABSTRACT

A method for assessing and displaying vasculature in a tissue mass using ultrasound and optimal velocity dependent data acquisition to differentiate between received signals from stationary tissue and received signals from slowly moving blood is disclosed herein. For a particular flow velocity, an optimal periodic or aperiodic signaling strategy is determined by matching the observation interval of any group of scatters to the correlated signal interval. Signals from moving blood cells are separated from signals from stationary tissue using a wall filter. Wall filtered signals from moving blood cells are further separated from signals from stationary tissue using a threshold filter. The resulting enhanced spatial and velocity resolution provides for identification of tumors by resistive index measurement, assessment of the percentage of vasculature in a section of tissue mass, and assessment of random structural characteristics, and further provides for three dimensional graphical display of vasculature within and surrounding a tissue mass.

26 Claims, No Drawings

METHOD FOR ASSESSING AND DISPLAYING VASCULAR ARCHITECTURE USING ULTRASOUND

This invention was made with Government support under Grant No. 1 R15 HL48273-01, awarded by the National Institutes of Health. The Government has certain rights in this invention.

BACKGROUND OF THE INVENTION

1. Field of the Invention

This invention pertains generally to ultrasonic diagnostic techniques, and more particularly to a method for assessing vascular architecture using ultrasound and displaying the vascular architecture in three dimensions to locate and identify tumors.

2. Description of the Background Art

Diagnostic ultrasonic techniques in medicine are of growing importance, because they are non-invasive, non-ionizing, and of low cost as compared to other sensing and imaging methods. As a result, ultrasound has been identified as a preferred non-invasive diagnostic tool for assessing the architecture of the vascular system in a human body for various medical purposes and, in particular, for locating tumorous tissue. It is well known that most, if not all, tumors are associated with an abnormal amount and pattern of vascular development. Therefore, it is desirable to use ultrasound for assessing the vasculature in human tissue. However, current ultrasound systems are not sufficiently sensitive to measure minute changes in the vasculature which are indicative of early tumorous development.

As a result of the need for accurate vascular imaging and identification of tissue abnormalities, various solutions for more accurate imaging have been proposed. For example, U.S. Pat. No. 5,243,988 issued to Sieben et al. on Sep. 14, 1993, discloses an invasive, intravascular imaging apparatus and methods for use and manufacture, for imaging small coronary vessels. U.S. Pat. No. 5,233,994 issued to Shmulewitz on Aug. 10, 1993, discloses a method for detection of tissue abnormality through blood perfusion between normal and tumorous tissue. U.S. Pat. No. 4,932,415 issued to Angelsen et al. on Jun. 12, 1990, discloses a method of color coding two dimensional ultrasonic doppler velocity images of blood flow on a display. U.S. Pat. No. 4,580,574 issued to Gavish on Apr. 8, 1986 discloses a method and device for non-invasively monitoring the instantaneous fluctuations in the viscoelastic-related properties of a living tissue. U.S. Pat. No. 4,542,744 issued to Barnes et al. on Sep. 24, 1985, discloses a method and apparatus for remote tissue identification by statistical modeling and hypothesis testing of echo ultrasound signals. U.S. Pat. No. 4,276,885 issued to Tickner et al. on issued Jul. 7, 1987, discloses methods for enhancing ultrasonic images. U.S. Pat. No. 4,074,564 issued to Anderson on Feb. 21, 1978, discloses a reconstruction system and method for ultrasonic imaging. U.S. Pat. No. 3,771,355 issued to Sachs on Nov. 13, 1973, discloses an ultrasonic inspection and diagnosis system.

Still, however, current practices and methodologies in ultrasound assessment of vascular architecture are limited due to inadequate resolution and sensitivity of the equipment. In particular, color flow imaging, which provides spatial velocity estimates for blood flow, is currently curtailed by the conflicting requirements of spatial and temporal resolution.

Therefore, there is a need for a method for assessing and displaying the vascular architecture in the a human body using ultrasound which is accurate and easy to use. More particularly, there is a need for a method of ultrasound imaging of vasculature which overcomes current limitations, particularly in the are of color flow mapping. The present invention satisfies that need, as well as others, and overcomes the deficiencies found in devices and techniques heretofore developed.

The foregoing patents reflect the state of the art of which the applicant is aware and are tendered with the view toward discharging applicant's acknowledged duty of candor in disclosing information which may be pertinent in the examination of this application. It is respectfully stipulated, however, that none of these patents teach or render obvious, singly or when considered in combination, applicant's claimed invention.

SUMMARY OF THE INVENTION

The present invention overcomes the deficiencies in current ultrasound imaging techniques by determining the optimal transmitted signal using the wideband maximum likelihood estimate (WMLE) as the optimal estimator for a particular range of blood flow velocities. By optimizing these parameters, particularly for slow flow, the method of the present invention provides for very high spatial resolution and vastly superior velocity discrimination for blood flow, thereby enabling early detection of malignant masses.

In general terms, the present invention comprises a method for transmitting, acquiring, processing, mapping, and displaying ultrasonic imaging data using a transducer to assess tumors. The method of the present invention provides for three dimensional mapping of the vasculature within and surrounding a solid mass. An important aspect of this method is the optimal acquisition of data which provides the opportunity to use a sensitive flow detection scheme that can differentiate between the received signal from stationary tissue and the received signal from very slowly moving blood. Due to the ability to differentiate small blood vessels from the surrounding tissue as a result of the present invention, measurements of the size and architecture of the vasculature can now be computed. Such measures were previously possible only through a gross histologic study after biopsy.

In accordance with the present invention, a tissue mass having a vasculature is subjected to wideband ultrasound imaging signals emitted from a transducer, and reflections of the ultrasound imaging signals from the tissue mass are then received using velocity dependent data acquisition. By differentiating between reflections of the ultrasound imaging signals from stationary tissue and reflections of the ultrasound imaging signals from slowly moving blood, the vasculature of the tissue mass is determined.

By way of example, and not of limitation, the method of the present invention includes the following steps:

1. For a particular flow velocity, an optimal periodic or aperiodic signaling strategy is determined by matching the observation interval of any group of scatterers to the correlated signal interval using velocity dependent data acquisition.
2. Signals from moving blood cells are separated from signals from stationary tissue using a wall filter.
3. Wall filtered signals from moving blood cells are further separated from signals from stationary tissue using a threshold filter.
4. Data acquisition is timed to the cardiac cycle, according to peak systole and mid diastole, and a resistive index (ratio of peak systolic velocity to mid diastolic velocity) is computed.
5. The volume of the detected vasculature is estimated.
6. A determination is made of changes in segment length and diameter as a function of branch order.
7. Space scale analysis and matching of the mean velocity of blood flow, blood vessel size, and blood vessel wall thickness are used to map the vascular tree based on multiple two dimensional views.
8. The vasculature is displayed using a three dimensional graphic display.

An object of the invention is to use ultrasound for early detection of malignant masses.

Another object of the invention is to create a map of the vasculature within and surrounding a solid mass.

Another object of the invention is to provide for differentiating between signals received from stationary tissue and those received from very slowly moving blood.

Another object of the invention is to measure the size and architecture of the vasculature with ultrasound.

Another object of the invention is to avoid the need for a gross histologic study after biopsy.

Further objects and advantages of the invention will be brought out in the following portions of the specification, wherein the detailed description is for the purpose of fully disclosing preferred embodiments of the invention without placing limitations thereon.

DESCRIPTION OF THE PREFERRED EMBODIMENTS

The following is a description of the preferred embodiments of the method for assessing and displaying vasculature architecture in accordance with the present invention. It will be appreciated, however, that the method of the present invention may vary as to specific steps and their sequence without departing from the basic concepts as disclosed herein.

In the present invention, a tissue mass is subjected to ultrasonic imaging signals by positioning a transducer above the subject. Wideband signals are then transmitted, received, and processed in accordance with the present invention. While other applications of the method disclosed herein are within the scope of the invention, it is contemplated that the method of the present invention be applied to assessing and displaying the vasculature in a human body. However, the method herein can be applied to assessing the vasculature in animal tissue as well. Further, the imaging signals are produced from a conventional ultrasound diagnostic apparatus or the like, and a single transducer can be used. The imaging signals used comprise pulses of ultrasonic beams transmitted by the transducer as well as the reflections of the pulsed beams received by said transducer. The beams have a lateral beam width, the transmitted signals have a center frequency and acoustic propagation velocity, and the received signals having a complex envelope.

1. Determining Optimal Signalling Strategy

The first step of the method of the present invention is to determine an optimal aperiodic or periodic signaling strategy for imaging the tissue mass by matching the observation interval of any group of scatterers to the correlated signal interval. This is accomplished using what is referred to herein as "velocity dependent data acquistion". Velocity dependent data acquistion has two essential facets, velocity dependent transmission (signalling) and velocity dependent signal processing after signal reception. The goal for the design of the signalling and estimation schemes is the sensitive estimation of low velocity flow, without producing an aliased estimate of rapid flow which may be present in a feed artery.

(a) Aperiodic Signalling.

Using an aperiodic signalling scheme with interleaved lines of sight a single data set is acquired over a long observation interval. Since the combined use of wideband transmission, wideband estimation with tracking of scatterers, and aperiodic signalling reduces the height of subsidiary velocity peaks and, therefore, the probability of an aliased estimate, a data set acquired with an aperiodic signalling strategy can be used to evaluate the likelihood of a wide range of velocities with a low probability of error. Using an interleaved periodic or aperiodic signalling scheme with a wideband maximum likelihood estimator (WMLE), a long observation interval can be used for each small spatial region without reducing the frame rate, or producing an aliased estimate. Thus the spatial and velocity resolution can be improved in comparison with existing systems.

In accordance with the present invention, the WMLE function for a discrete velocity value v, corresponding to a two way travel time d, is preferably determined in according with the following equation (1):

$$l(v) = \left| \sum_k \int_{-\infty}^{\infty} r'(t) s_0'^*(t - d - kT[1 + 2v/c]) \exp[j2 w_c vt/c] dt \right|^2 \quad (1)$$

where:

C=acoustic propagation velocity;

l(v)=likelihood of velocity v;

r'(t)=complex envelope of the received signal;

T=period of the transmitted pulse;

$S_o'(t)$=deterministic portion of the received complex signal envelope;

v=axial velocity of the estimator;

$w_c$=center frequency of the transmitted signal (radians/second);

d=two way travel time;

k=pulse train index; and t=time.

Note also that the presence of v within the envelope matches the change in delay, and that the presence of v within the exponential matches the frequency shift of the red blood cells. Therefore, the likelihood involves the sum over the pulse train indexed by k, and the integral over the temporal axis, t. The integrand is the product of the complex envelope of the received signal, an estimate of the complex envelope of the received signal being denoted by $s_o'(.)$, and the Doppler shift.

The optimal signalling scheme requires a strategy which permits line interleaving, which sets the temporal difference between the first and last pulse equal to the limit of signal stationarity for slowly moving scatterers, and finally minimizes the height of subsidiary velocity peaks given the first two constraints. The limit of signal stationarity is equal to the transit time through the lateral beam width for the smallest velocity of interest at a beam vessel angle of 45 degrees, or a limit of cardiac stationarity, shown through previous research to approximately equal 10 ms. A pulse train of 18 pulses with a total duration from the first to last pulse of 10 ms has been shown through experimentation to be sufficient to detect a range of velocities from 1 mm/s to 20 cm/s using the velocity dependent estimation strategies. Using 18 pulses with 6 pulses reserved for clutter rejection, the remaining 12 pulses can be used to generate the velocity estimate. Under these constraints, a pulsing scheme which uses a pulse to pulse separation of 2 to 8 times the pulse repetition period as the pulse to pulse interval along an individual line of sight produces aliased peaks of acceptable height (small probability of error), provides for pulse to pulse interleaving, and uses the approximate total time interval.

Using an 8 kHz pulse repetition rate and pulse to pulse interleaving, one such scheme which produces sensitivity to flow of 1 mm/s or less is uses the signal from the following pulses with the first pulse indexed as 0:

{0,2,4,10,16,18,20,26,32,34,36,42,48,50,52,58}

A second sequence which improves the sensitivity to low velocities, at the cost of a small increase in the number of aliased peaks is:

{0,6,14,20,22,28,36,42,44,50,58,64,66,72,80,86,88,94}

Additionally, fixed signal components are rejected. This is critical in order to assess early development of tumors. While advanced tumors will exhibit high flow rates, early tumors will exhibit very slow flow rates which must be distinguished from vessels having normal flow. Those skilled in the art will appreciate that other pulse indices could be utilized in this scheme provided that slow flow velocities are detectable.

(b) Periodic Signalling.

An alternate methodology for velocity dependent transmission is periodic signalling. Periodic signalling eliminates errors from aliased velocities at the cost of an increase in the time over which data is collected. Here, a set of pulses are transmitted at a periodic pulse repetition rate which is chosen to eliminate aliased estimates at the highest velocity of interest to the likelihood or correlation estimator.

When using this scheme to map the vascular architecture of a mass, several pulse repetition rates would be used, with the pulse repetition period increasing as the possibility of high velocities is eliminated. Increasing the pulse repetition period increases the sensitivity of the estimate to low velocities. For example, using a 7.5 MHz transducer, assuming that the maximum possible velocity in the central feed artery to a mass size of 1.5 cm$^3$ is 30 cm/s, the maximum pulse repetition frequency is 11688 Hz (acoustic velocity/ (2×center frequency×scatterer velocity)). The maximum velocity to a mass can be assumed from previous clinical experience, or determined by a preliminary scan from a conventional instrument. A set of 18 pulses would be transmitted at this frequency and the likelihood or correlation for velocities below 30 cm/s would be evaluated. Assuming that the peak velocity detected is 10 cm/s, a second set of pulses would be transmitted with a pulse repetition rate of 3896 Hz (11688/3). This second set of data would be significantly more sensitive to the presence of low velocity flow.

(c) Velocity Dependent Signal Processing.

After transmitting and receiving the ultrasound imaging signals using an optimal aperiodic or periodic signalling scheme as described above, the received signals are processed using velocity dependent signal processing. For processing each velocity of interest, the duration of the correlated signal is used to determine the length of the signal which should be combined coherently. The correlated signal interval is estimated using each velocity and a beam vessel angle of 45 degrees with a maximum of 10 ms imposed by the cardiac stationarity when the ability to follow changes in the mean velocity over the cardiac cycle is desired. Thus, the correlated signal interval is given by:

$$CSI = LB/(VTBE) \quad (2)$$

where:
CSI=correlated signal interval;
LB=lateral beam width; and
VTBE=velocity to be evaluated using likelihood or correlation strategies.

Using this processing method, color flow maps of velocities ranging from 0.8 mm/s to 5 cm/s have been generated. Further, the use of the velocity dependent strategy decreased the variance of the velocity estimate by a factor of 4 using the WMLE at higher velocities. As a result, the accuracy and sensitivity of this scheme are significantly improved from conventional systems.

While the WMLE minimizing scheme is preferred, cross-correlation could also be used for velocity dependent data acquisition. In accordance with the present invention, a preferred cross-correlation function is represented as:

$$C(t, t-\tau) = \sum_k \sum_m \int_{t-W/2}^{t+W/2} r_k(t') r_m(t'+\tau) dt' \quad (3)$$

where:
k=pulse train index;
m=pulse train index;
W=width of window;
t=time;
$r_k(t')$=baseband return from kth pulse; and
$r_m(t')$=baseband return from mth pulse.

2. Wall Filtering

Next, a wall filter is used to separate signals reflected from moving blood cells from signals reflected from stationary tissue. Assessment of flow through a tumor requires the detection of flow velocities of several mm/s or less, in the presence of a signal from the stationary tissue which can be 40 db larger. Conventional systems are unable to detect any flow in many regions, including normal breast tissue or small tumor sites, due to the inability to differentiate signals from stationary tissue from those reflected by slowly moving blood. Therefore, improved detection of tumors requires the use of a sensitive wall filter to differentiate between signals reflected from stationary tissue and those reflected from slow moving blood.

The wall filter in accordance with the present invention is specifically designed for the detection of very slow flow through small vessels in the presence of rapid flow with a maximum velocity of approximately 10 cm/s; and for the separate use of the two signals which are generated by the structure. Two estimators for the tissue component, $r_{fd}(u-d)$, at a delay d are used, where each is estimated for each axial sample. Each estimate is based on the average over the pulse train of the returned signal. Both have been tested for this particular situation and found to have significant advantages. In the first case, the average is computed over the group of pulses to be used in an estimate. In the second case, the average is computed over the group of P pulses which immediately follow any particular pulse. The second strategy requires the transmission of several extra pulses on each line of sight, but eliminates any velocity bias. In either case the estimate can be written as:

$$r_{fd}(t-d) = 1/P \sum_m r'(t-d-mT) \quad (4)$$

The signal from the moving scatterers, $r_{ms}$, is then separated by subtraction from the total signal:

$$r_{ms}(t-d) = r'(t-d) - r_{fd}(t-d) \quad (5)$$

In this approach to a sensitive wall filter both components, the fixed signal and the moving signal components, are used to find the position of small vessels, and are used in the reconstruction.

3. Threshold Filtering

After further filtering with a conventional clutter rejection filter, a threshold filter operation is performed in order to determine whether the wall filtered signal represents moving red blood cells or residual noise. First, the threshold, which can be varied under operator control, is preferably determined jointly by the magnitude of the likelihood function and the post wall filtered power. When either the normalized magnitude of the likelihood or the post wall filtered power falls below the threshold, the tissue is considered to be stationary. This method provides greatly superior results over conventional systems which use only the wall filtered power for the threshold; while the wall filtered power is an adequate measure when assessing rapid flow, it is not adequate for slow flow.

In the preferred embodiment, the normalized magnitude of the likelihood function is compared to an established threshold which is typically 0.65, and the un-normalized post wall filtered power is compared to an operator set threshold. The result of these two operations is then combined with a logical "and" operation which must be satisfied for flow to be detected.

In accordance with the present invention, the normalized likelihood function is determined as the ratio of the likelihood, l(v), to the wideband power threshold, lp, which is based on the summed power in the moving window. Where the wideband power threshold, lp, is defined as:

$$lp = \sum_k \left| \int_{-\infty}^{\infty} r'(t) s_0'^*(t - d - kT[1 + 2v/c]) dt \right|^2 \quad (6)$$

the normalized likelihood, nl(v), is $$nl(v) = \quad (7)$$

$$\frac{\left| \sum_k \int_{-\infty}^{\infty} r'(t) s_0'^*(t - d - kT[1 + 2v/c]) \exp[j2\omega_c vt/c] dt \right|^2}{\sum_k \left| \int_{-\infty}^{\infty} r'(t) s_0'^*(t - d - kT[1 + 2v/c]) dt \right|^2}$$

The post wall filtered power, which is also referred to as the narrowband noise threshold, np, and which is based on the summed power in the windowed signal, is defined as:

$$np = \sum_k \left| \int_{-\infty}^{\infty} r'(t) a'^*(t - d - kT) dt \right|^2 \quad (8)$$

where:

a'(t) = is the axial window applied to the signal received from an individual pulse.

Alternatively, the threshold operation could be based on the ratio of the cross correlation magnitude to the correlation power threshold, denoted nC(t,t+τ) according to:

Normalized Correlation 1

$$nC(t, t-\tau) = \frac{\sum_k \sum_m \int_{t-W/2}^{t+W/2} r_k(t') r_m(t'+\tau) dt'}{\sum_k \sum_m \left| \int_{t-W/2}^{t+W/2} r_k(t') r_m(t'+\tau) dt' \right|} \quad (9)$$

or

Normalized Correlation 2

$$nC(t, t-\tau) = \frac{\sum_k \sum_m \int_{t-W/2}^{t+W/2} r_k(t') r_m(t'+\tau) dt'}{\sum_k \sum_m \int_{t-W/2}^{t+W/2} |r_k(t') r_m(t'+\tau) dt'|} \quad (10)$$

A typical threshold for either type of normalized correlation is 0.75. It has been found, however, that Normalized Correlation 1 provides the most accurate results of the correlation functions.

A still further alternative would be to use narrowband autoregressive strategies applied to the magnitude of the second order poles $$|P_1| \text{ and/or } |P_2| \quad (11)$$

which is typically 0.8.

As can be seen, therefore, the normalization factor is chosen to estimate the power in the summed pulse sequence. Experimental tests of the foregoing threshold operators in a complex flow field have shown significantly improved performance when using the WMLE with the normalized likelihood as a threshold operator. Using this operator with in-vivo data, a reliable distinction between tissue and flow could be made on the basis of this threshold operation alone. This produced significant advantages in the mapping of a complex flow field. Using this normalized quantity to distinguish tissue from flow, as opposed to the filtered power, the threshold operation is not affected by attenuation. In addition, this operator was superior to any form of the normalized correlation, which includes cross signal terms. The normalized correlation incorrectly detected flow in regions of a tissue mimicking material which exhibits periodicity in the density of the scatterers.

4. Timing Data Acquisition To Cardiac Cycle And Determining Resistive Index

Due to the enhanced spatial and velocity resolution which results from the foregoing steps, in-vivo estimates of tissue parameters which could previously be determined only by biopsy can be made. For example, by timing data acquisition to the cardiac cycle according to peak systole and mid diastole, a resistive index (ratio of peak systolic velocity to mid diastolic velocity) can be computed and used to differentiate between normal and malignant masses. Tumor vessels are more elastic and less muscular than healthy tissue and, therefore, the ratio of the peak systolic velocity to the mid diastolic velocity is less. In other words, a drop in the resistive index indicates a malignant tissue. Therefore, the resistive index of scanned tissue can be compared to a threshold, or compared to the resistive index from adjacent tissue to identify a drop indicative of a tumor. Current ultrasound color flow mapping systems do not provide the opportunity to develop a color flow map for particular portions of the cardiac cycle. In addition, such systems cannot accurately assess the flow at mid-diastole in small vessels and therefore cannot accurately assess the resistive index.

5. Determining Volume of Detected Vasculature

In addition, due to the enhanced spatial and velocity resolution of the this method, an accurate estimate of the volume of the detected vasculature can be made by estimating individual vessel volume and integrating over the individual volume. An abnormal mass shows a larger percentage of vasculature and, therefore, the volume estimate can be used to detect tumors. In contrast, conventional systems rely on an estimate of the proportion of pixels within an image, which contain flow, and are not sufficiently sensitive to differentiate normal and abnormal tissues.

6. Determining Changes and Segment Length and Diameter

Also, a determination can be made of changes in segment length and diameter as a function of branch order. Again, due to the enhanced spatial and velocity resolution of the foregoing method, an accurate assessment of the changes in the segment length and diameter as a function of branch order can be determined. These parameters become random in a malignant mass.

7. Space Scale Analysis

Next, space scale analysis and matching of the mean velocity of blood flow, blood vessel size, and blood vessel wall thickness is used to reconstruct the vascular tree based on multiple two dimensional views. The use of these three parameters in the reconstruction is unique. The architecture is expected to display random boundaries when malignant. In addition a larger malignant mass is expected to demonstrate a necrotic core (no vessels) surrounded by a region of hypervascularization.

8. Displaying Detected Vasculature

Finally, the vasculature is visually displayed using a three dimensional graphic display, based on interpolation using B-splines and similar geometrical interpolation algorithms.

Accordingly, it will be seen that this invention provides for accurate and effective assessment and display of vascular architecture using ultrasound, and can provide information which has heretofore been available only through biopsy and gross histologic study of a tissue sample. Early detection of tumors is made possible by the present invention through the use of ultrasound in a non-invasive manner. Using the method of the present invention, spatial and velocity resolution is enhanced to levels which permit identification of tumors by resistive index measurement, assessment of the percentage of vasculature in a section of tissue mass, assessment of random structural characteristics. Further, for the first time it is possible to provide for three dimensional graphical display of vasculature within and surrounding a tissue mass.

Although the description above contains many specificities, these should not be construed as limiting the scope of the invention but as merely providing illustrations of some of the presently preferred embodiments of this invention. Thus the scope of this invention should be determined by the appended claims and their legal equivalents.

We claim:

1. A method for assessing the vascular architecture of a tissue mass using ultrasound imaging, comprising the steps of:

(a) subjecting a tissue mass to wideband ultrasound imaging signals emitted from a transducer using velocity dependent signalling, said tissue mass having a vasculature;

(b) receiving reflections of said ultrasound imaging signals from said tissue mass and processing said reflections using velocity dependent signal processing;

(c) differentiating between reflections of said ultrasound imaging signals from stationary tissue and reflections of said ultrasound imaging signals from slowly moving blood; and (d) identifying the vasculature of said tissue mass from said reflections of said ultrasound imaging signals.

2. A method as recited in claim 1, further comprising the step of matching observation intervals of scatterers with correlated signal intervals for the duration of coherence of said ultrasound imaging signals.

3. A method as recited in claim 1, further comprising the step of differentiating between reflections of said ultrasound imaging signals from stationary tissue and reflections of said ultrasound imaging signals from slowly moving blood using a wall filter.

4. A method as recited in claim 3, further comprising the step of differentiating between reflections of said ultrasound imaging signals from slow moving blood and reflections of said ultrasound imaging signals from stationary tissue using a threshold filter.

5. A method as recited in claim 1, further comprising the steps of:

(e) timing data acquisition to cardiac cycle according to peak systole and mid diastole; and (f) determining a resistive index based on the ratio of peak systolic velocity to mid diastolic velocity.

6. A method as recited in claim 1, further comprising the step of estimating the volume of said vasculature.

7. A method as recited in claim 6, further comprising the step of identifying abnormal tissue based on said estimated volume of said vasculature.

8. A method as recited in claim 1, further comprising the steps of constructing a vascular tree using space scale analysis and matching of mean velocity of blood flow.

9. A method as recited in claim 1, further comprising the step of displaying said vasculature using a three dimensional graphic display.

10. A method for locating a tumorous tissue mass using ultrasound, comprising the steps of:

(a) subjecting a tissue mass to wideband ultrasound imaging signals emitted from a transducer using velocity dependent signalling, said tissue mass having a vasculature;

(b) receiving reflections of said ultrasound imaging signals from said tissue mass and processing said reflections using velocity dependent signal processing;

(c) differentiating between reflections of said ultrasound imaging signals from stationary tissue and reflections of said ultrasound imaging signals from slowly moving blood; and (d) identifying and assessing the vasculature of said tissue mass from said reflections of said ultrasound imaging signals.

11. A method as recited in claim 10, further comprising the step of matching observation intervals of scatterers with correlated signal intervals for the duration of coherence of said ultrasound imaging signals.

12. A method as recited in claim 11, further comprising the step of differentiating between reflections of said ultrasound imaging signals from stationary tissue and reflections of said ultrasound imaging signals from slowly moving blood using a wall filter.

13. A method as recited in claim 12, further comprising the step of differentiating between reflections of said ultrasound imaging signals from slow moving blood and reflections of said ultrasound imaging signals from stationary tissue using a threshold filter.

14. A method as recited in claim 13, further comprising the steps of:

(e) timing data acquisition to cardiac cycle according to peak systole and mid diastole;

(f) determining a resistive index of said tissue mass based on the ratio of peak systolic velocity to mid diastolic velocity; and (g) sensing a drop in said resistive index, said drop being indicative of a tumor.

15. A method as recited in claim 13, further comprising the steps of:

(e) estimating the volume of said vasculature; and (f) assessing the percentage of vasculature in said tissue mass, said percentage being indicative of a tumor.

16. A method as recited in claim 13, further comprising the steps of:

(e) constructing a vascular tree using space scale analysis and matching of mean velocity of blood flow;

(f) identifying random boundaries of said vascular tree, said random boundaries being indicative of a tumor; and (g) locating a necrotic core surrounded by an area of hypervascularization in said tissue mass, said necrotic core being indicative of a tumor.

17. A method as recited in claim 10, further comprising the step of displaying said vasculature using a three dimensional graphic display.

18. A method for assessing vasculature in living tissue using ultrasound imaging and velocity dependent data acquisition, comprising the steps of:

(a) subjecting a tissue mass to wideband ultrasound imaging signals emitted from a transducer using velocity dependent signalling, said tissue mass having a vasculature;

(b) receiving reflections of said ultrasound imaging signals from said tissue mass using velocity dependent signal processing;

(c) matching observation intervals of scatterers with correlated signal intervals for the duration of coherence of said ultrasound imaging signals;

(d) separating reflections of said ultrasound imaging signals from stationary tissue and reflections of said ultrasound imaging signals from slowly moving blood using a wall filter;

(e) separating reflections of said ultrasound imaging signals from slow moving blood and reflections of said ultrasound imaging signals from stationary tissue using a threshold filter; and (f) determining the vasculature of said tissue mass from said reflections of said ultrasound imaging signals.

19. A method as recited in claim 18, further comprising the step of displaying said vasculature using a three dimensional graphic display.

20. A method as recited in claim 18, further comprising the steps of:

(g) timing data acquisition to cardiac cycle according to peak systole and mid diastole;

(h) determining a resistive index of said tissue mass based on the ratio of peak systolic velocity to mid diastolic velocity;

(i) estimating the volume of said vasculature;

(j) assessing the percentage of vasculature in said tissue mass; and (k) constructing a vascular tree using space scale analysis and matching of mean velocity of blood flow.

21. A method for assessing the vascular architecture of a tissue mass using ultrasound imaging, comprising the steps of:

(a) subjecting a tissue mass to wideband ultrasound imaging signals emitted from a transducer using velocity dependent signalling, said tissue mass having a vasculature;

(b) receiving reflections of said ultrasound imaging signals from said tissue mass and processing said reflections using velocity dependent signal processing;

(c) timing data acquisition to cardiac cycle according to peak systole and mid diastole;

(d) determining a resistive index based on the ratio of peak systolic velocity to mid diastolic velocity;

(e) differentiating between reflections of said ultrasound imaging signals from stationary tissue and reflections of said ultrasound imaging signals from slowly moving blood; and (f) identifying the vasculature of said tissue mass from said reflections of said ultrasound imaging signals.

22. A method for assessing the vascular architecture of a tissue mass using ultrasound imaging, comprising the steps of:

(a) subjecting a tissue mass to wideband ultrasound imaging signals emitted from a transducer using velocity dependent signalling, said tissue mass having a vasculature;

(b) receiving reflections of said ultrasound imaging signals from said tissue mass and processing said reflections using velocity dependent signal processing;

(c) differentiating between reflections of said ultrasound imaging signals from stationary tissue and reflections of said ultrasound imaging signals from slowly moving blood;

(d) identifying the vasculature of said tissue mass from said reflections of said ultrasound imaging signals; and (e) constructing a vascular tree using space scale analysis and matching of mean velocity of blood flow.

23. A method for locating a tumorous tissue mass using ultrasound, comprising the steps of:

(a) subjecting a tissue mass to wideband ultrasound imaging signals emitted from a transducer using velocity dependent signalling, said tissue mass having a vasculature;

(b) receiving reflections of said ultrasound imaging signals from said tissue mass and processing said reflections using velocity dependent signal processing;

(c) matching observation intervals of scatterers with correlated signal intervals;

(d) differentiating between reflections of said ultrasound imaging signals from stationary tissue and reflections of said ultrasound imaging signals from slowly moving blood using a wall filter and a threshold filter;

(e) identifying and assessing the vasculature of said tissue mass from said reflections of said ultrasound imaging signals;

(f) timing data acquisition to cardiac cycle according to peak systole and mid diastole;

(g) determining a resistive index of said tissue mass based on the ratio of peak systolic velocity to mid diastolic velocity; and (h) sensing a drop in said resistive index, said drop being indicative of a tumor.

24. A method for locating a tumorous tissue mass using ultrasound, comprising the steps of:

(a) subjecting a tissue mass to wideband ultrasound imaging signals emitted from a transducer using velocity dependent signalling, said tissue mass having a vasculature;

(b) receiving reflections of said ultrasound imaging signals from said tissue mass using velocity dependent signal processing;

(c) matching observation intervals of scatterers with correlated signal intervals;

(d) differentiating between reflections of said ultrasound imaging signals from stationary tissue and reflections of said ultrasound imaging signals from slowly moving blood using a wall filter and a threshold filter;

(e) identifying and assessing the vasculature of said tissue mass from said reflections of said ultrasound imaging signals;

(e) estimating the volume of said vasculature; and (g) assessing the percentage of vasculature in said tissue mass, said percentage being indicative of a tumor.

25. A method for locating a tumorous tissue mass using ultrasound, comprising the steps of:

(a) subjecting a tissue mass to wideband ultrasound imaging signals emitted from a transducer using velocity dependent signalling, said tissue mass having a vasculature;

(b) receiving reflections of said ultrasound imaging signals from said tissue mass and processing said reflections using velocity dependent signal processing;

(c) matching observation intervals of scatterers with correlated signal intervals;

(d) differentiating between reflections of said ultrasound imaging signals from stationary tissue and reflections of said ultrasound imaging signals from slowly moving blood using a wall filter and a threshold filter;

(e) identifying and assessing the vasculature of said tissue mass from said reflections of said ultrasound imaging signals.

(f) constructing a vascular tree using space scale analysis and matching of mean velocity of blood flow;

(g) identifying random boundaries of said vascular tree, said random boundaries being indicative of a tumor; and (h) locating a necrotic core surrounded by an area of hypervascularization in said tissue mass, said necrotic core being indicative of a tumor.

26. A method for assessing vasculature in living tissue using ultrasound imaging and velocity dependent data acquisition, comprising the steps of:

(a) subjecting a tissue mass to wideband ultrasound imaging signals emitted from a transducer using velocity dependent signalling, said tissue mass having a vasculature;

(b) receiving reflections of said ultrasound imaging signals from said tissue mass and processing said reflections using velocity dependent signal processing;

(c) matching observation intervals of scatterers with correlated signal intervals;

(d) separating reflections of said ultrasound imaging signals from stationary tissue and reflections of said ultrasound imaging signals from slowly moving blood using a wall filter;

(e) separating reflections of said ultrasound imaging signals from slow moving blood and reflections of said ultrasound imaging signals from stationary tissue using a threshold filter;

(f) determining the vasculature of said tissue mass from said reflections of said ultrasound imaging signals;

(g) timing data acquisition to cardiac cycle according to peak systole and mid diastole;

(h) determining a resistive index of said tissue mass based on the ratio of peak systolic velocity to mid diastolic velocity;

(i) estimating the volume of said vasculature;

(j) assessing the percentage of vasculature in said tissue mass; and (k) constructing a vascular tree using space scale analysis and matching of mean velocity of blood flow.

* * * * *